United States Patent [19]

Tronzo

[11] Patent Number: 4,743,262
[45] Date of Patent: May 10, 1988

[54] ACETABULAR CUP PROSTHESIS

[76] Inventor: Raymond G. Tronzo, 255 Clarke Ave., Palm Beach, Fla. 33480

[21] Appl. No.: 29,849

[22] Filed: Mar. 24, 1987

Related U.S. Application Data

[63] Continuation-in-part of Ser. No. 616,100, Jun. 1, 1984, Pat. No. 4,681,589.

[51] Int. Cl.[4] .............................................. A61F 2/34
[52] U.S. Cl. ...................................................... 623/22
[58] Field of Search ..................................... 623/16-23

[56] References Cited

U.S. PATENT DOCUMENTS

| | | | |
|---|---|---|---|
| D. 276,463 | 11/1984 | Hamm | 623/22 |
| 3,641,590 | 2/1972 | Michele | 623/22 |
| 3,685,058 | 8/1972 | Tronzo | 623/22 |
| 3,808,606 | 5/1974 | Tronzo | 623/22 |
| 3,840,904 | 10/1974 | Tronzo | 623/22 |
| 4,566,138 | 1/1986 | Lewis et al. | 623/22 |

FOREIGN PATENT DOCUMENTS

| | | | |
|---|---|---|---|
| 2411617 | 4/1975 | Fed. Rep. of Germany | 623/22 |
| 2621667 | 11/1977 | Fed. Rep. of Germany | 623/18 |
| 2950536 | 7/1981 | Fed. Rep. of Germany | 623/22 |
| 3129174 | 2/1983 | Fed. Rep. of Germany | 623/22 |
| 3205527 | 8/1983 | Fed. Rep. of Germany | 623/22 |

OTHER PUBLICATIONS

"The Art of Total Hip Arthroplasty" by Dr. William T. Stillwell; Grune and Stratton, Inc. 1987; p. 5.

Primary Examiner—Richard J. Apley
Assistant Examiner—David J. Isabella
Attorney, Agent, or Firm—Eugene Chovanes

[57] ABSTRACT

Fins on a hip prosthesis implant for anchoring the implant in good bone. The fins may be integral with, or separately attachable to, the implant. The fins extend radially outwardly beyond the perimeter of the implant from the front face longitudinally rearward.

8 Claims, 4 Drawing Sheets

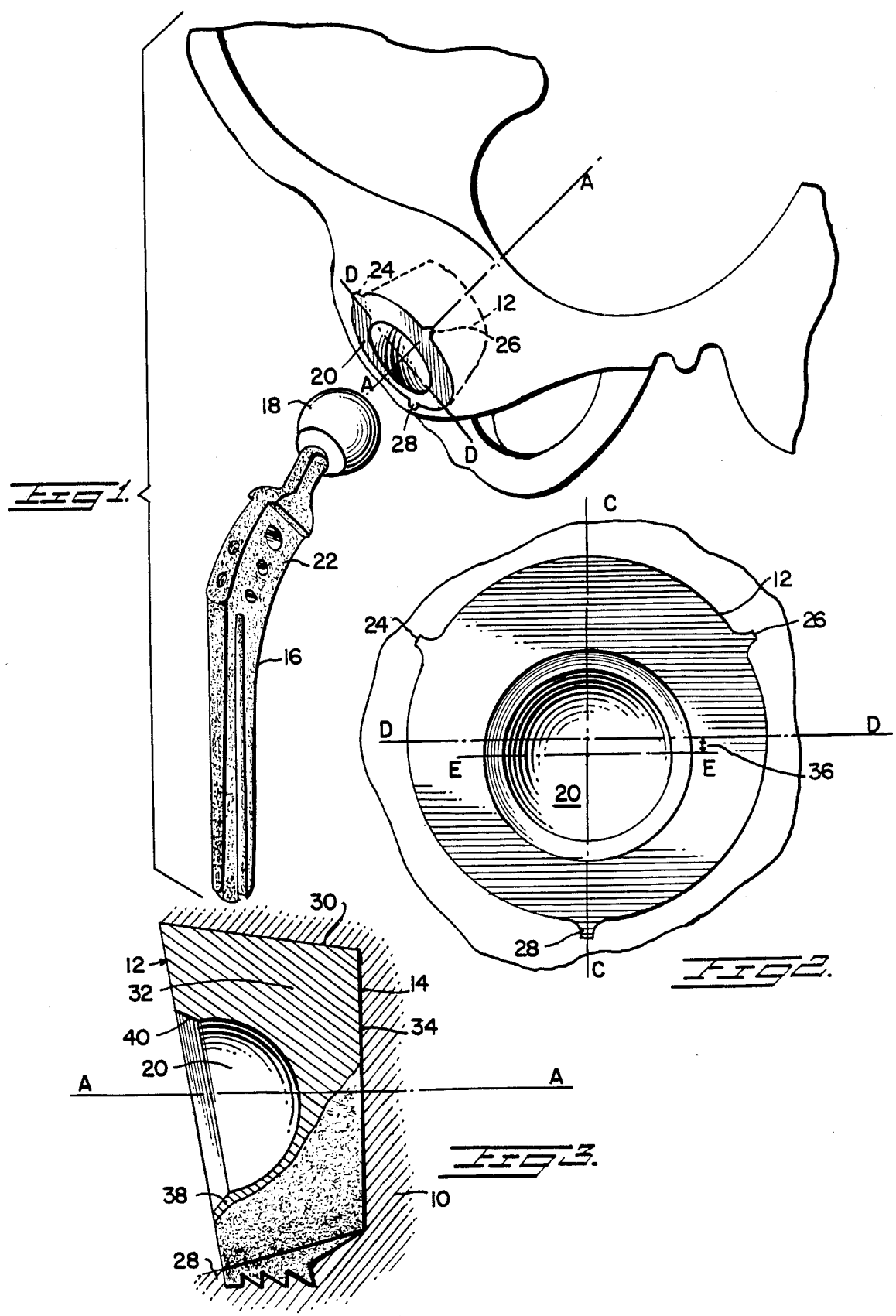

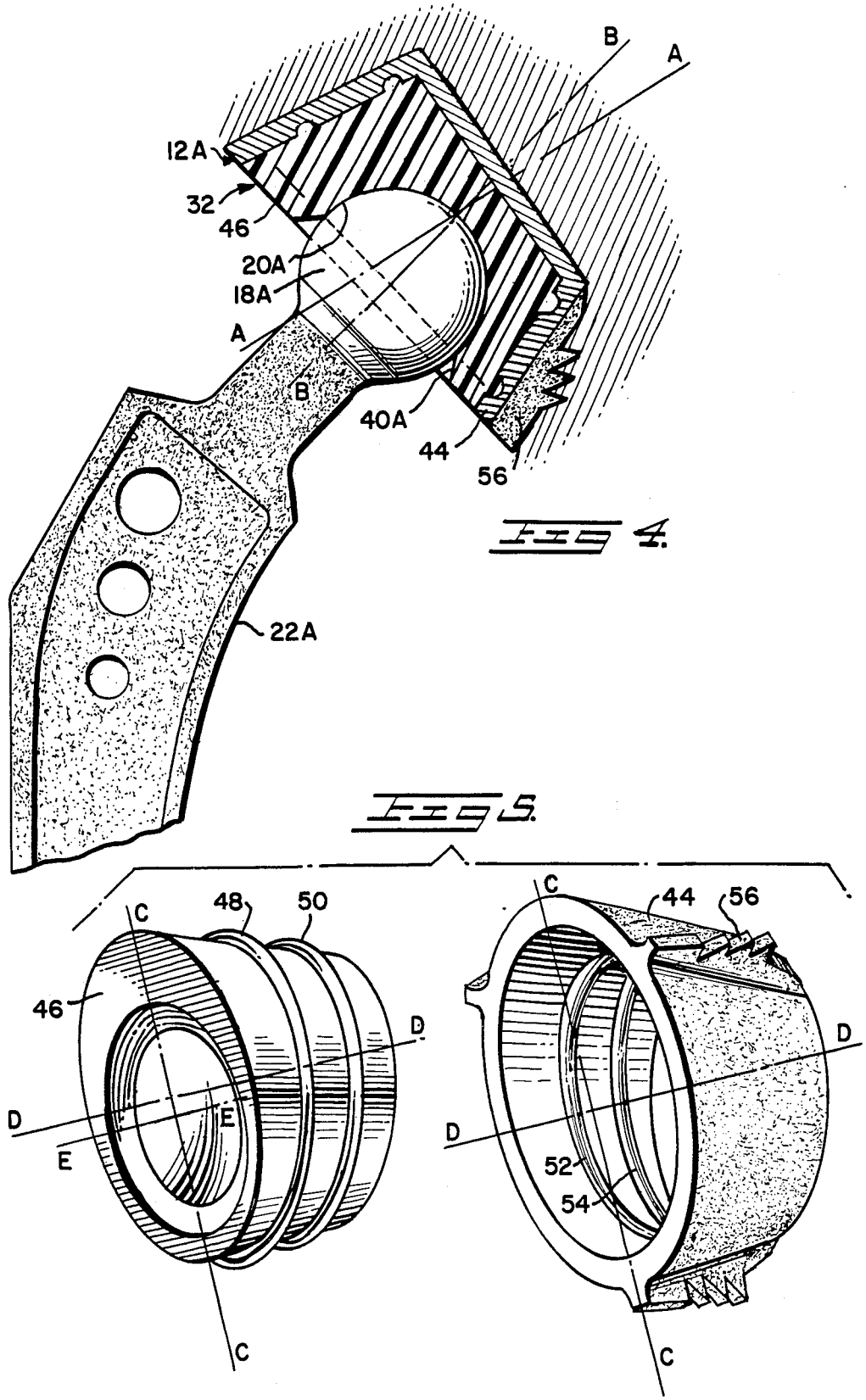

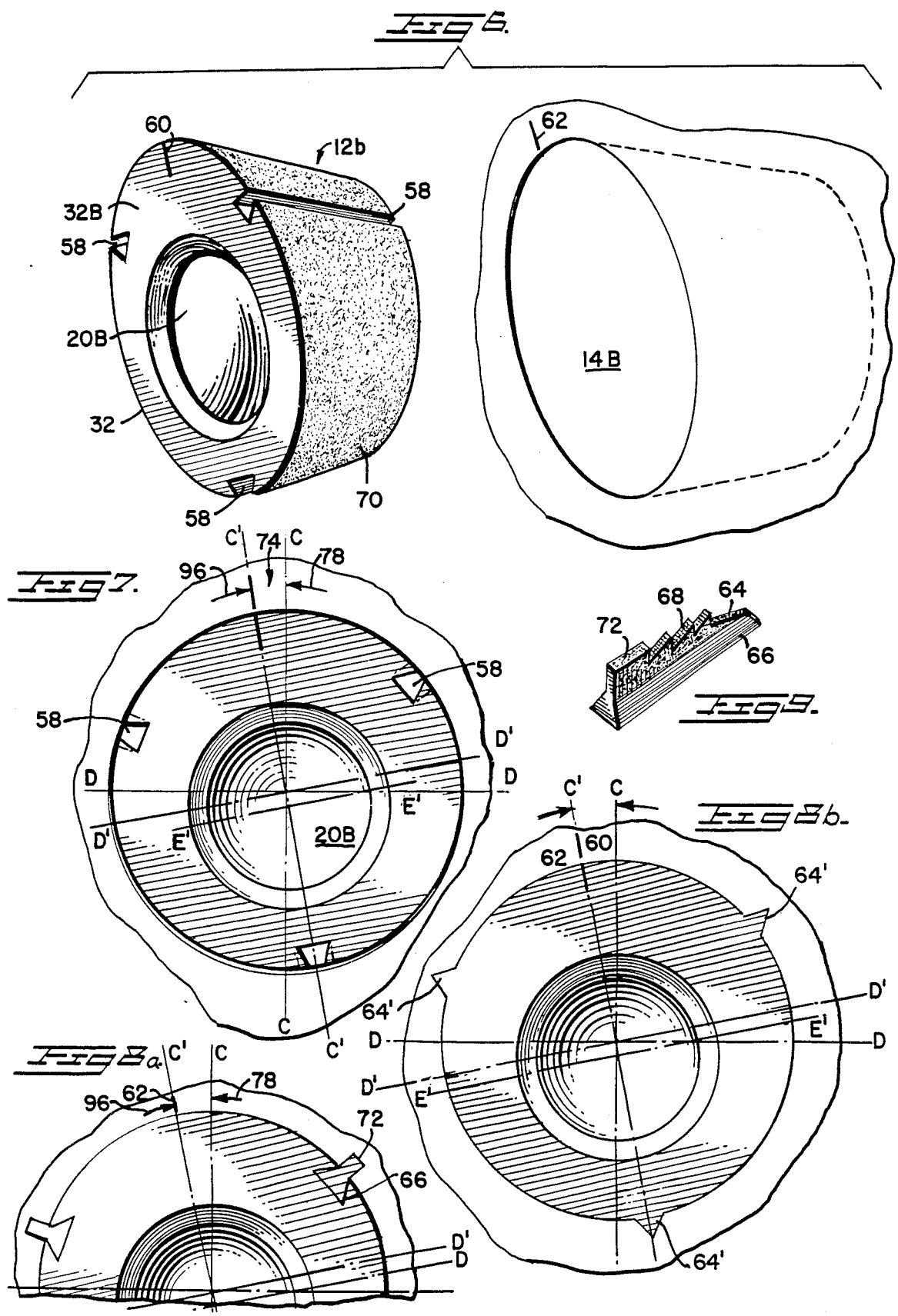

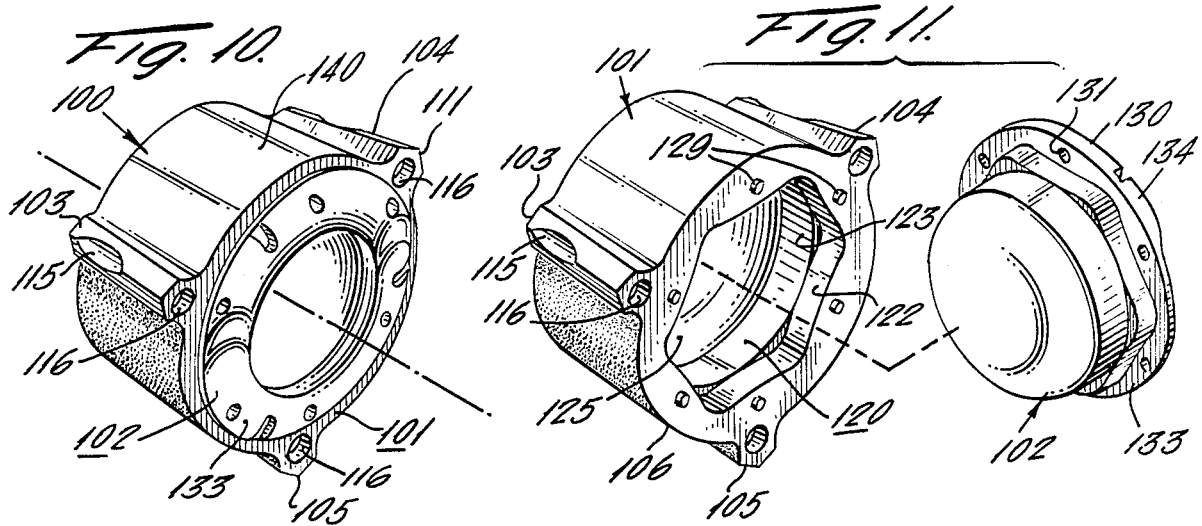
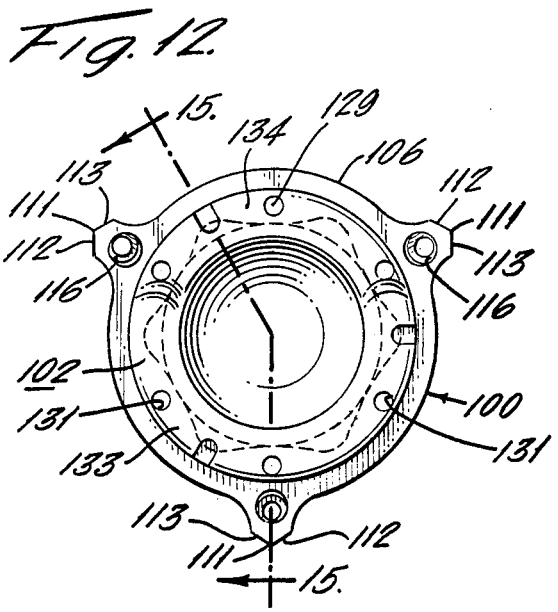
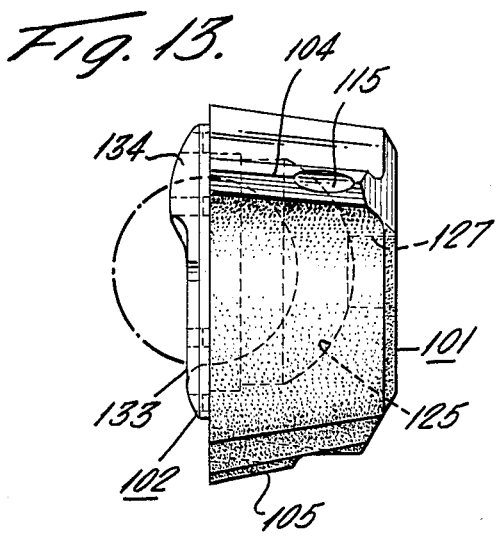
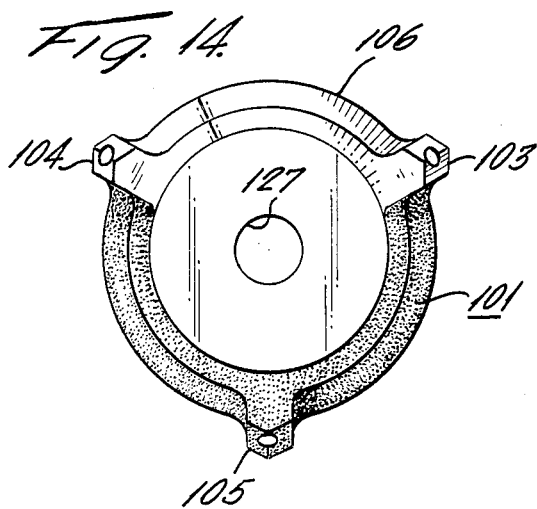
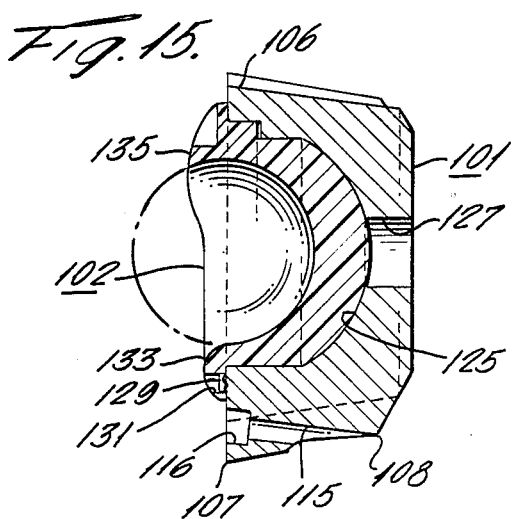

ACETABULAR CUP PROSTHESIS

This is a continuation-in-part of my co-pending application Ser. No. 616,100 filed June 1, 1984 now U.S. Pat. No. 4,681,589, for ADJUSTABLE ACETABULAR CUP PROSTHESIS AS PART OF A TOTAL CUP REPLACEMENT SYSTEM.

FIELD OF THE INVENTION

The present invention relates to total hip joint prosthesis of a type including an acetabular cup implant adapted for insertion in an acetabular bone, and which has a femoral ball on a femoral pin, the ball being positionally mounted within a usual ball socket in a cup implant.

Such constructions are well known in the art and exemplary of such constructions as those disclosed in my prior U.S. Pat. Nos. 3,840,904 of Oct. 15, 1974 and 3,808,606 of May 7, 1974.

The disclosures in my prior patents are incorporated herein by reference thereto for purposes of delineating an art area within which the present invention is usable. Other constructions and devices are also existing in the prior art and it is a primary purpose of the present invention to provide a new and improved design or concept for such a hip prosthesis and preferably of a total hip prosthesis.

The present invention includes features which provide for an initial positional fixation in the hip bone of a user which will facilitate optimum interaction of a femoral ball within an articulating socket in the acetabular implant, both initially and over an extended period of use by the user.

Other meritorious features will appear hereinafter in descriptions of preferred embodiments of the invention.

BACKGROUND OF THE INVENTION

Total hip joint prosthesis of a type including an acetabular cup implant provided with a ball socket for mounting operationally a femoral ball on a femoral pin are knon in the art.

Some problems have existed in the prior art devices for various reasons.

It is sometimes difficult to obtain an initial and lasting relative positionment of the socket in the implant so that the ball will continue optimally functional in use regardless of positional movement or rotation of the user's leg.

The acetabular cup implant of the present invention, and as also shown in my prior U.S. patents and in devices of others in the art, have included position maintaining means such as spikes or blades or hemispheroidal devices designed to hold the implant firmly in place while resisting rotational, compressive, and distracting forces on the implant during an initial phase of bony ingrowth and subsequent fixation with respect to the bone opening in which placed. Means to relatively fix the components over a long time have additionally included use of a porous surface or coated cup design to facilitate a normal growth of bone into fixation in and with respect to the openings in the porous surface.

In combination, the heretofore used spikes or other fixation means and the porous surface have provided relatively favorable results in use.

Certain drawbacks have existed, however, in prior known devices both as regards the initial positionment of the cup within which the femoral head is rotatably mounted or contained, and initial and lengthy fixation of the acetabular cup with respect to the bone within which implanted devices have not been entirely satisfactory. As pointed out above, certain steps have heretore been utilized to provide a friction fixation for a primary initial fixation and a secondary or continuing arrangement or means wherein the specific outer porous surfaces of the cup intergrows with the bone for a long-range fixation. This broad combination of concepts is known in the art. The present invention, however, provides new and highly improved results in construction and use of the hip prosthesis as distinguished from the prior art and the results obtained provide a most desirable initial and continuing living connection or interconnection between the implant and the bone which is indepedent of any sizing of the porous oversurface.

It will also be noted that the present invention is usable in such a manner that the acetabular cup with the ball socket can be positionally moved subsequent to the initial positionment in a bore provided in the bone so that the implanting position can insure optimum alignment with the femoral ball or head on a femoral pin regardless of position or use of a leg of the user and will prevent a disconnection (or dislocation) between these two portions of a prosthesis.

Also as will be apparent from the following disclosure, the so-adjustable cup implant can be provided with fins which can either be permanent or which can be placeable with respect to the implant following positionment thereof, these fins being longitudinally positioned with respect to the axis of the implant. The total external surface of the implant and/or the longitudinal fixation fins can have a porous or pore arrangement which will provide the desirable initial and continuing living connection between the implant and the bone. It can also be left bare of any porosity and left to remain fitted into its final position by a friction-fit alone, although the bony ingrowth mode of fixation will be the preferred one.

Anchoring elements in various forms are known in the prior art. For instance, in my aforementioned U.S. Pat. Nos. 3,808,606 and 3,840,904, and in U.S. Pat. No. 3,528,199 there are shown anchoring spikes. U.S. Pat. No. 3,641,590 uses drifts or pins. The present device differs from these prior art cups in that the fins, or outriggers, of the present invention extend generally longitudinally rewardly of the body of the cup from the front face, and extend diametrically radially beyond the perimeter of the body at the front face.

While certain forms of the present invention will be specifically shown and described hereinafter, obviously the invention is not limited to the specific structures and variations disclosed but will permit of obvious variations within the scope of the invention as defined by the claims herein.

Other and additional meritorious features and advances in the art will be apparent from the following disclosure.

BRIEF DESCRIPTION OF THE DRAWINGS

The accompanying drawings illustrate preferred embodiments of the invention, and when taken together with the following description, serve to explain the principles and structures of the invention.

DETAILED DESCRIPTION OF THE FIGURES

FIG. 1 is an exploded perspective view of the present invention as utilized in a total hip joint prosthesis replacement procedure;

FIG. 2 is a front elevational view showing an acetabular cup in accordance with the present invention;

FIG. 3 is a side elevational view, partially broken away, to show the femoral ball cup implant and the interrelationship thereof with a femoral ball, and as procedurally positioned in a hip bone implant receiving bore;

FIG. 4 is an assembly view, partially in cross section, of the components in FIG. 1, showing a modified form thereof incorporating a plastic insert in the hip socket implant to facilitate improved interaction therebetween;

FIG. 5 is an exploded perspective view of the components constituting the hip cup implant shown in FIG. 4.

FIG. 6 is an exploded perspective view of a hip socket implant and relationship to the opening formed in the hip bone prior to insertion of the socket implant;

FIG. 7 is a front elevational view, similar to FIG. 2, of a modified form of a socket implant, and disclosing an adjusted positionment relative to the opening in the hip bone as shown in FIG. 6. This is better identified as a "Trial Cup." It can be rotated to the optimal position with notches provided for marking the bone for final insertion of the fins or blades.

FIG. 8a is a fragmentary view similar to FIG. 7, and showing the device as being secured in its adjusted position;

FIG. 8b is a view similar to FIG. 7, and showing a modified fin form 64' as a portion of the cup;

FIG. 9 is a perspective view of one of the securing fins employed in FIG. 8a, as an optional mode of fixating the cup in place.

FIGS. 10 through 15 inclusive show another embodiment of the device of the invention.

FIG. 10 is a perspective view of an embodiment showing still further the concept of fins or outriggers outside the circumference of the implant.

FIG. 11 is an exploded perspective view showing the metallic implant with its inner plastic liner removed.

FIG. 12 is a front elevational view of the device shown in FIG. 10, again showing the fins or outriggers extending beyond the outer circumference of the implant.

FIG. 13 is a right side elevational view of the device of FIG. 12

FIG. 14 is a rear elevational view of the device of FIGS. 10 through 13.

FIG. 15 is a stepped section taken on the line 15,15 of FIG. 12, showing in greater detail and insert.

SUMMARY OF THE INVENTION

The Present Invention (Broadly)

The total hip joint prosthesis of the present invention broadly includes an acetabular cup implant adapted for placement in a prebored opening or hole in a patient's hip socket and this acetabular cup implant can be of a construction permitting its placement within the bore, and operable for an initial adjustable positioning thereof for optimum interaction with a prosthetic femoral ball or head mounted on the usual femoral prosthesis. The ball socket or opening in the implant or cup can, by rotation of an acetabular cup, define or reveal to the installing physician the optimum position of the socket to coact with the femoral ball or head regardless of the positional disposition of a patient's leg, for example. Such an acetabular cup which can be positionally rotated can be referred to as a test implant or trial implant, and such a final construction, if desired, can include the external surface porosity to facilitate intergrowth of bone structure therewith, and further the construction can provide for a plurality of positionally fixing fins mountable on the external surface of the acetabular implant following the attainment of the optimal position of the implant and ball socket. In other words, the trial cup could serve two purposes; (1) as a trial cup allowing it to be rotated into an ideal position and, (2) once so positioned, could remain in place while the fins are driven into the bone along the slotted paths (FIG. 6 and FIG. 9) ending up as in FIG. 8. The test cup can be otherwise devised for use by the implanting physician or surgeon, by rotation, and by use of indicia means on the cup or implant to permit the physician to make an installation marking adjacent the bore in the patient's hip. The test implant can then be withdrawn and replaced by an implant which includes all of the structural features including the porous exterior surface and the fixing fins, with optionally plain or porous external surfaces, and containing an indicia for matching up with the indicia adjacent the bone bore to insure appropriate placement of the acetabular cup implant in the patient.

Another and extremely important aspect of the present device resides in the configuration of the acetabular cup as a trapezoid or a portion of a truncated cone. As has been noted over a period of time, bones or bone structure in users of hip prosthesis of the type of the present inventon have a certain degree of small amount of shrinkage, technically called "demineralization" or "physiological atrophy." This shrinkage has, in some prior art devices, caused a disjoinder or migration of the acetabular cup in the patient's or user's hip and there has been a tendency for separation of divorcement or painful loosening of the cup from the user's hip bone. The trapezoidal configuration of the present invention is devised to compensate for such shrinkage of the bone and maintain dynamic press positioning. It is also known that the inner surface or socket in the bone may be diseased and/or distorted from previous surgical procedures. The present device serves to exploit a bleeding inner surface, once appropriately prepared surgically, without the necessity of removing the fragile tissue while at the same time permitting the insertion of the device so that it will not rotate but will also grip the good, hard outer bone. The implant, due to its configuration, will react dynamically rather than as a static member. As bone, subsequent to placement of the implant, tends to retract or withdraw from the implant to a small degree, but nevertheless going through a shrinking action, which in the prior art caused loosening of the implant eventually had been overcome by the present device. The present design, i.e., the trapezoidal or conical shape, provides a mechanism whereby the implant structure and accommodate any such shrinking, constantly providing a dynamic and vital bony contact which aids the secondary connection and growth in the porous surface, as known in the art, into the bone for longevity of the combination in the patient's hip joint.

Hence, the physical configuration and design of the cup works constantly with bony growth around the cup to provide any necessary compensating movement, while at the same time providing the optimum initial placement and positioning fixation required for a continuing optimal intercoaction of the parts and proper structural support in a firm and rigid manner. Apropos of this, the present concept or invention differs completely from the blades as shown, for example, in prior U.S. Pat. No. 3,840,904, since in the present invention, the crux of the matter is that movement can take place longitudinally of the cup, in effect translation to compensate for the bone change due to shrinkage while at the same time preventing rotation and providing a continuing secure connection. These features substantially diminish the necessity of subsequent removal of prosthesis installations from patients wherein a deterioration of bone, and/or integration between the implant and the bone has occurred. Bone movement in a physiological manner is compensated for, which keeps the bone-metal contact a healthy, continuous interdigitation between bone and implant, to provide a basis for long-range, living connection.

THE PRESENT INVENTION (SPECIFICALLY)

Fins or outriggers, either integral with the implant, or attached separately, or both, are used in combination with the implant. These fins or outriggers extend diametrically radially beyond the periphery of the implant from the face of the implant, longitudinally rearward. The fins or outriggers secure the implant in sound bone beyond the periphery of the implant.

In one form of the invention, the implant has a body, a cavity within the body, and an adjustable removable insert.

The body portion of the implant can have a spherical, conical, trapezoidal, or other suitable outer surface. The outer surface can be porous or plain. The fins or outriggers can be serrated or smooth.

The body can have screw-in threads on the outer surface, wherein separately attached fins or outriggers are inserted after the body is screwed in place, whereby the screwed-in body is fixed rotatively and longitudinally.

The fins or outriggers may have a smooth exterior, or they may be coated with a porous, or rough substance.

The fin or outriggers may be self cutting into the bone, or self-broaching.

The fins or outriggers may have transverse holes therethrough to further permit bone growth into the holes to aid further anchoring.

The fins or outriggers may be three in number, spaced equally circumferentially, or a greater number. Some may be integral with the body, and some may be attached after the implant is in place.

In all instances, the fins or outriggers extend generally diametrically radially beyond the periphery of the implant, at the front face, and extend, from the front face, longitudinally rearward.

DESCRIPTION OF THE PREFERRED EMBODIMENT

Referring now specifically to the drawings, FIG. 1 discloses in an exploded perspective view the structure contemplated by the invention and indicating usage thereof in a prosthesis of a person as a substitute or artificial replacement unit. In this figure, the pelvis of a prospective user or patient is indicated fragmentarily at 10. An acetabular cup implant is broadly indicated at 12 and is shown as being positioned in a bore or hole shown by dotted lines at 14 in the hip bone 10. As will be noted from the broken line showing of the cup at 14, the shape is trapezoidal or a portion of a cone. This is more clearly shown in other figures. The configuration of the implant 12 is more clearly shown in the fragmentary sectional view thereof in FIG. 3. FIG. 3 shows the eccentric nature of the cup, the top or superior lip being shorter than the bottom or inferior lip. This eccentricity allows a trail cup, as will be described later, to be rotated in the bony socket until the ideal position has been found as a "stable articulation" between ball and socket. Alternatively, the cup could be true with all sides being equal.

In FIG. 3, the bore 14 is also more clearly shown as being commensurate with the size and shape of the implant cup 12 and is so drilled or formed in hip bone 10 by the surgeon who is to implant the prosthesis. Referring again to FIG. 1, a femoral pin 16, as known in the art, structurally supports a femoral head or ball 18 at its upper end, and which is adapted for mating operational engagement within socket 20 in implant cup 12. It is to be noted that the external surface of the pin 16 is provided with a porous coating at 22. This porous coating is known in the art and serves the function of facilitating bone growth thereinto for permanent affixation of the member with respect to the user's bone, also as well known in the art. The material of the pin can differ, as also can the material of the femoral head 18 all as well known in the art. In one possible combination, the cup is all metal while the femoral ball may be likewise metal, but could be plastic, or a ball of ceramic articulating with a ceramic cup of this special design configuration. The material of head 18 preferably should be of a high grade plastic or metal composition to insure long lasting and non-deteriorated affixation functionally within socket 20. Head size and socket size are variable.

The inner cup or liner 14 can likewise be formed from different materials although a preferable one, as shown in FIG. 1, consists of a high grade plastic or porcelain, while the outer cup is made out of steel or steel alloys or titanium or titanium alloys. Attention is also invited to a plurality of longitudinally extended fins 24, 26 and 28. These fins will be discussed in greater detail hereinafter as regards their construction and function. Initially however, it is to be noted that these fins are positioned at spaced intervals around the outer periphery of the cup, being three as shown in the drawings. This can vary. It is also to be noted that these fins extend lonngitudinally of the implant cup; i.e., parallel to the axis or center line B—B of the socket 20. The fins can, as will appear hereinafter, be permanent with respect to the implant cup or can be removably mounted thereto. The external face of the fins is provided with a plurality of teeth indicated at 32, or may be plain as an option, or perforated with holes. When the implant is placed in the prepared bony bore and driven into engagement into such bore in a known manner, these fins serve the functional purpose of preventing rotation of the cup within the bore and additionally the teeth aid in preventing displacement longitudinally of the cup with respect to the bore and bone as will be readily understood, as added supplemental fixation for overall seating of the implant into the patient's socket.

Referring again to FIGS. 1 through 3 of the drawings, it is pointed out that the bore or hole 14 is drilled into the bone along a lne A—A as distinguished from the center line B—B of socket 20; special cutting tools or reamers are used.

One outstanding feature of the present invention resides in the configuration of the cup implant 12. By reference particularly to FIG. 3, it will be seen that the external shape of this member 12 constitutes a portion of a truncated cone. The cup includes a front face 32 and a rear face 34. The front face 32 is not at right angles to the line or axis C—C while face 34 is at right angles to A—A, which also constitutes the longitudinal axis of the socket 20. Line B—B is perpendicular to the inner socket 20.

Referring now to FIG. 2 of the drawings, it will be seen that the socket 20 has a center on line E—E which is displaced from the center line D—D of the implant 12. This displacement is indicated by an arrow 36 in FIG. 2. The result is that the cup 20, and front face 38 thereof, are eccentric with respect to the line of rotation of the cup and longitudinal center line D—D. Rotation of the cup will cause eccentricity of movement of the socket longitudinally and through an arc. A chamfered surface 40 is provided at the opening of socket 20 for the purpose of facilitating easy insertion and movement of head or ball 18 within the socket 20.

In the showing of FIGS. 1 through 3, the fins 24 are integral with the external periphery of the implant 12 and the implant is driven into engagement as one piece within the bore or hole 14 and this position is maintained by means of the fins engaging in the material of the hip bone 10 exterior to the bore. The angular disposition of pin 16, head 18 and socket 20 are such that normal disposition or movement of a user's leg with respect to the individual members of the total hip prosthesis are as normal as possible and will cover and be operable in all normal positions of the patient's leg.

In FIG. 4, a modification of the invention is shown. The femoral ball may be preferably metal to articulate with the plastic socket. The implant cup 12A includes an outer metal, or other material, shell 44 which has mounted therein a plastic material insert 46. The plastic insert is provided with a plurality of rings 48 and 50 on the external surface for connection and mating engagement within internal rings or grooves 52, 54 in the interior surface of shell 44. The shell may be molded into permanent positioning or may be removed by a variety of standard mechanical methods. A chamfer 40A is provided in this modification and the external surface of the outer shell 44 is provided with a plurality of integrated fins of the same character and construction as fins 24–28 in FIG. 1. They serve the same function and are similarly arranged. The axes A—A; B—B; C—C; D—D and E—E in FIGS. 4 and 5 are similar to those shown in the embodiment of FIGS. 1, 2 and 3. The operation of this embodiment will accordingly be similar.

A further modification of the invention is disclosed in FIG. 6. In this embodiment, the acetabular implant cup 12B includes the same external trapezoidal configuration and includes a socket 20B eccentrically disposed in the front face 32B. In this embodiment, a plurality of grooves 58 are provided in the external surface of the implant and are longitudinally disposed. The grooves are configured as dovetailed members. An indicia mark 60 is included on the front face 32B. In effect, this embodiment of the invention can constitute a so-called dual device, a test implant unit which could be fixed into final position by fins driven along the slots or grooves in its side walls, as referred above, and can be placed within the bore or hole 14B which is similar to 14 in FIG. 1. In use the cup test unit 12B can be positionally rotatably displaced in the bore by the inserting surgeon. The eccentricity of positioning of the sockets 20, 20A and 20B will, in conjunction with the slanted front face 32, serve to rotate, together with the implant, the orientation of the sockets with respect to the bore in which inserted. It is to be noted and of substantial importance that the opening and socket will, upon rotation of the implant, have bidirectional movement, one being arcuate about the rotational axis and the opening face of the socket will be longitudinally moved slightly inward or outward due to the angular disposition of face 32.

In use of the modification shown in FIG. 6, once the surgeon has appropriately disposed the implant for optimum coaction of the ball and socket he will make a positioning indicia mark 62 in the bone surrounding the bore 14B. At that time, the test unit can be permanently fixed in place by driving fins such as seen in FIG. 9 into position.

Another possibility when utilizing the embodiment of FIG. 6 is to orient the implant in the bore and thereafter to insert in the bores 58 separate fins 64 shown in FIG. 9 and which include tapered bases 66 for connection with the dovetail configuration of grooves 58. These fins, again, are toothed at 68 similar to the teeth 29 in FIG. 3. By driving these separate fins into place in the positioned implant, the implant will be fixed. The external surfaces of the implant at 70 and the fin at 72 are porous as in the other embodiment.

The inserting manipulation and repositioning of the socket and the axis thereof for optimal intercoaction with the femoral head on the femoral pin will be more readily understood from FIGS. 7 and 8. Utilizing the embodiment of FIG. 6 as the test positioning unit, the implant 12B is positioned by the surgeon to the optimum position for co-action with the ball, the position indicator 62 being marked by reference to indicator mark 60, the axis C—C having been rotated from an initial to ultimate position through the angle indicated at 74 between arrows 76, 76 and the axis D—D being moved to the position D'—D' as shown in FIGS. 7 and 8. In this operation, the test unit 12B can either have been removed and replaced by the unit shown in FIG. 1 or FIG. 4 or the test unit of FIG. 6, after placement and rotation or orientation can have had the fins as shown in FIG. 9 driven thereinto for fixation of the implant in the bore. A modified groove configuration is shown in phantom lines in FIG. 7.

DESCRIPTION OF THE EMBODIMENT OF FIGS. 10 THROUGH 15

As seen in FIGS. 10 through 15, an implant 100 comprises a body 101 and an insert 102. The body 101 is suitably of a metallic inert alloy material such as alloy steel, as well known in the art. The insert 102 can suitably be of a high strength polyethylene, for instance.

The body 101 is of a truncated conical general configuration as described heretofore. As shown in FIGS. 10 through 15 particularly, there are a plurality of fins or outriggers 103, 104 and 105. The body 101 has an outer perimeter 106 as best seen in FIGS. 12 and 14. fins or Outriggers 103, 104 and 105 extend radially outwardly substantially beyond the perimeter 106, and are spaced at an angle of 120° from one another. The fins or outriggers extend approximately the full depth of the truncated cone body 101 from the front face at 107 to a back face at 108.

Each of the fins or outriggers 103, 104 and 105 extend longitudinally of the body 101 but, as set forth immediately above as well as earlier in the description of the previous embodiments, the outriggers extend radially beyond the perimeter 106.

The outriggers have, on their radially outward surface, an apex 111 formed of converging sides 112 and 113.

In addition, the outriggers, 103 through 105 are optionally bored at 115 to receive screws outside the circumference of the truncated cone as seen in FIG. 15. The bore 115 has a countersunk section 116. These screws could engage bone grafts used to build up any missing positions of the socket.

The body 101 has formed therein a central cavity 120 which is of a shape comprising a series of geometric configurations, disposed one to another, the outermost being of a generally hexagonal configuration in a transverse view of the implant, as shown particularly in FIG. 11. Such hexagonal portion is indicated at 122. An adjacent portion within the cavity 120 is of a circular shape in transverse section, again as seen in FIG. 11. Such circular portion is designated at 123.

Immediately adjacent such circular section, is a tangential hemispherical bottom portion designated 125, terminating in a centrally located bore 127 as clearly seen in FIG. 15.

Indexing pins 129 are suitably integral with body 101 and centrally and axially spaced with respect to the hexagon portion 122.

The insert 102 has portions complementary to the cavity portions of body 101. More particularly, a shoulder portion 130 having first a large diametrical circumferentially extending ring portion 130 which lies adjacent the front face 107 of the body 101 in position thereon, has spaced holes or indentations 131 which mate with and receive pins 129. Also on the outer face of circumferentially extending ring portion 130 are three slots spaced 120° apart angularly for the positioning and to aid insertion of the insert 102 within body 101 in cavity 120.

As shown in FIGS. 10 and 12, the insert 102 is illustrated as being in a test position prior to final positioning which may or may not be in the test position. The outer rim 130 is of a non-uniform, cross-sectional shape having a relatively thin lower section 133 extending angularly through approximately 250° as seen in FIG. 12 and in FIG. 10.

A thicker section 134 extends along the upper periphery for approximately the remaining 110° angle, as shown in FIGS. 15, 13 and 10, forming a shoulder 135.

It should be understood that cavity 123 and insert 102 each have a longitudinal axis, although in the embodiment shown, the axis of the insert and the cavity are coincidental at all angular positions. The shoulder 135 can be formed to have an inner thickness greater at one circumferential position that at another, so that by rotation of the insert within the cavity, the orientation of the longitudinal axis of the insert can be altered angularly with respect to the longitudinal axis of the cavity. This is in the manner described earlier by a screw arrangement in FIG. 5 wherein the pocket is eccentric. The cup in FIG. 10 can likewise be eccentric as shown in FIG. 5 and related views.

The recessed portion or thin portion 133 of insert 130 permits clearance for the stem of the ball portion of an artificial hip implant to provide free articulation with no interference. This was described before as to the articulation in FIG. 4 in the description relative to FIG. 4 and more particularly FIG. 1.

Shoulder 135 also forms an overhang which serves to retain the ball of the implant in the cavity, wherein the ball can be snapped in or forced into the cavity with somewhat of force fit.

The embodiment shown in FIG. 10 particularly emphasizes and illustrates clearly the function and importance of fins or outriggers 103, 104 and 105 which were disclosed above and described earlier with respect to the embodiments set forth. The fins or outriggers 103, 104 and 150, as well as the fins or outriggers shown in the earlier embodiments, sit outside the perimeter of the body of the implant which, as seen in FIGS. 10 through 15, is a truncated cone. It should be understood the body alternatively can have a semi-circular external shape, or another suitable shape which could use the fins or outrigger concept disclosed herein. In all body shapes, however, there will be a front face and the fins or outriggers will extend from the front face rearwardly longitudinally. The important feature is that the fins or outriggers are positioned diametrically outwardly beyond the perimeter of the body, for the front face rearwardly, longitudinally. The fins or outriggers may extend rearwardly to the back face, or may terminate at a point short of the back face. The fins or outriggers are very advantageous for gripping bone outside of the perimeter of the bed of bone that is cut away by instruments for inserting the implant. By means of the fins or outriggers, bone is gripped outside of the implant area to lock the prosthesis in place. Once in place, the fins or outriggers provide resistance to rotation of the implant and, second, allow bony ingrowth in areas of bone that are not necessarily accessible by the coventional systems. This is especially true where previous implants have failed. In such cases, the acetabulum or socket is quite distorted. When an effort is made to sculpt out a new bed for a replacement implant, bone often is not avilable within the perimeter so made. With the fins or outriggers of the present invention, one may go outside of the perimeter to locate good bone, in, for instance, a procedure called "revision arthroplasties."

The present fins or outriggers can be integral with the body of the implant as shown in FIGS. 10 through 15 inclusive, or they can be detachable and driven into place as a secondary procedure as shown in FIGS. 6, 7, 8 and 9. Although three are shown for the purpose of illustration, there can be any suitable number. Where detachable fins or outriggers are used, longitudinal slots can be made successively around the entire circumference as shown in FIG. 6, and then the fins or outriggers can be positioned in place.

There is also illustrated the feature in FIGS. 10 through 15 of the rim 130 on the insert 102. This rim can be turned or rotated in various directions. This is an alternative to the embodiment shown in the earlier figures. In some of these embodiments, the cup was sloped, making the opening eccentric whereby it can be rotated into advantageous positions. in the present cup insert, the insert can be rotated after the body 101 is inserted. Also, the removable insert can be replaced at a future date if it wears out. The insert is fixed in place by flat sides 122.

Additionally, in the embodiment of FIGS. 10 through 15, the fins or outriggers can be bored as shown so that screws can be threaded into bone to further fix the implant. By virtue of the fins or outriggers, structure is available outside the implant periphery, to bore out to receive screws so that the screws may grip the bone outside of the perimeter.

Additionally, the screws can be optionally placed in bores that are drilled at diverging angles, so that the implant with the fins or outriggers can be inserted in a longitudinal direction with respect to the longitudinal axis of the implant, and then screws can optionally be angled whereby an even broader circumference can be attained with respect to bone anchors.

The implant units can be different sizes and materials and the fins or outriggers can be specifically different so long as the orientation thereof is longitudinal, extending from the front face, and they serve to grip the outer solid bone as hereinbefore described.

While preferred embodiments of the invention have been shown in the drawings and described herein, manifestly minor variations therein will be obvious to those skilled in the art without departing from the spirit of the invention. Such obvious changes or modifications are considered to be within the scope of the inventive concept as expressed herein, and as claimed hereinafter.

I claim:

1. An acetabular cup prothesis comprising a body extending generally longitudinally and terminating into front and rear surfaces, said front surface extending substantially transversely to said body; and at least one fin for securing said cup to a prepared acetabulum cavity, said fin having a length extending generally longitudinally from said front surface toward said rear surface continuously along said body throughout the entire length of said fin, and said fin being configured so as to extend radially outwardly beyond the perimeter of said front surface and said body so as to engage with the cavity thereby securing said cup.

2. An implant of claim 1, wherein the body has a generally conical outer surface.

3. An implant of claim 1, wherein the body has a generally hemispherical outer surface.

4. An implant of claim 1, wherein the body has threads on its outer surface.

5. An implant of claim 1, wherein the implant has a porous outer surface.

6. An implant of claim 1, wherein the fins are integral with the body.

7. An implant of claim 1, wherein each of the fins has a bore adapted to receive an anchoring screw.

8. A device of claim 7, wherein the longitudinal axis of the bore diverges outwardly rearwardly with respect to the longitudinal axis of the body whereby the screw can be anchored in bone radially outward from the fin.

* * * * *

REEXAMINATION CERTIFICATE (2303rd)

United States Patent [19]
Tronzo

[11] B1 4,743,262
[45] Certificate Issued May 17, 1994

[54] ACETABULAR CUP PROSTHESIS

[76] Inventor: Raymond G. Tronzo, 255 Clarke Ave., Palm Beach, Fla. 33480

Reexamination Request:
No. 90/002,666, Mar. 2, 1992

Reexamination Certificate for:
Patent No.: 4,743,262
Issued: May 10, 1988
Appl. No.: 29,849
Filed: Mar. 24, 1987

Related U.S. Application Data

[63] Continuation-in-part of Ser. No. 616,100, Jun. 1, 1984, Pat. No. 4,681,589.

[51] Int. Cl.⁵ .............................................. A61F 2/34
[52] U.S. Cl. ................................................... 623/22
[58] Field of Search .............................. 623/22, 23, 18

[56] References Cited

U.S. PATENT DOCUMENTS

4,450,592  5/1984  Niederer et al. .

FOREIGN PATENT DOCUMENTS

0038903   2/1981   European Pat. Off. .
0058753  10/1981   European Pat. Off. .
0058753   7/1985   European Pat. Off. .
2159416A 12/1985   United Kingdom .

OTHER PUBLICATIONS

Biomet, Inc. Brochure, "Mallory-Head Total Hip Program," Feb. 7, 1986.

*Primary Examiner*—David J. Isabella

[57] ABSTRACT

Fins on a hip prosthesis implant for anchoring the implant in good bone. The fins may be integral with, or separately attachable to, the implant. The fins extend radially outwardly beyond the perimeter of the implant from the front face longitudinally rearward.

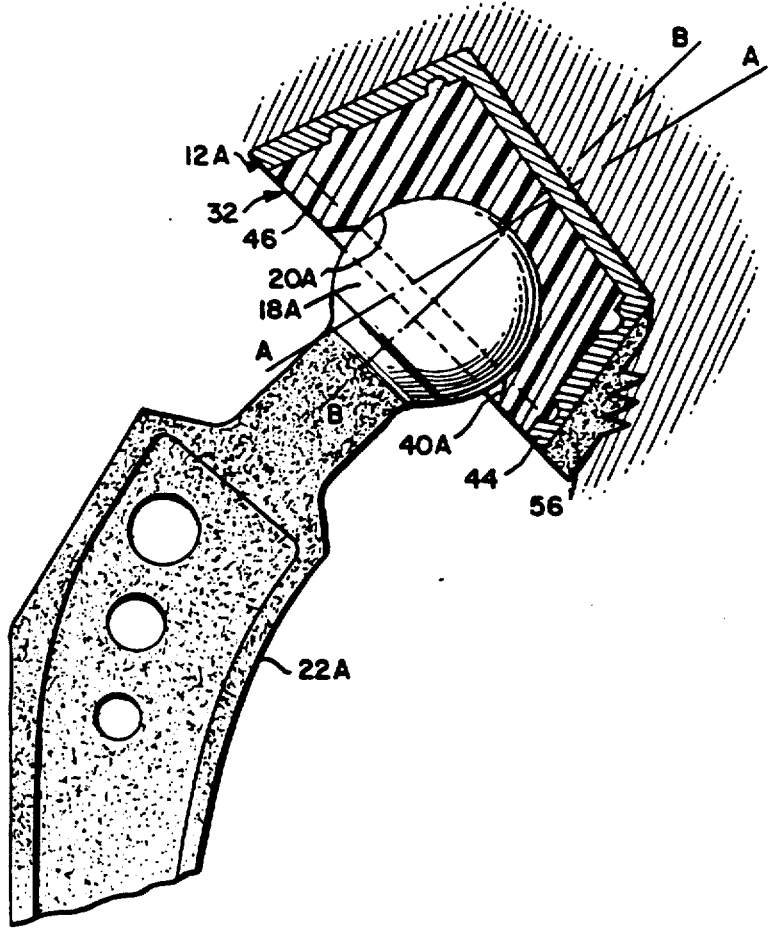

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1-8 is confirmed.

New claims 9-11 are added and determined to be patentable.

9. *An acetabular cup prosthesis consisting essentially of (1) a body extending generally longitudinally and terminating into front and rear surfaces extending substantially transversely to said body; and (2) at least one fin for securing said cup to a prepared acetabulum cavity, said fin having a length extending generally longitudinally from said front surface toward said rear surface continuously along said body throughout the entire length of said fin, and said fin being configured so as to extend radially outwardly beyond the perimeter of said front surface and said body so as to engage with the cavity thereby securing said cup.*

10. *A prosthesis of claim 9, wherein the body has a generally conical outer surface.*

11. *A prosthesis of claim 9, wherein the body has a generally hemispherical outer surface.*

* * * * *